(12) United States Patent
Jeong et al.

(10) Patent No.: US 11,113,944 B2
(45) Date of Patent: Sep. 7, 2021

(54) WALKING ANALYSIS APPARATUS AND METHOD

(71) Applicant: ELECTRONICS AND TELECOMMUNICATIONS RESEARCH INSTITUTE, Daejeon (KR)

(72) Inventors: Min Gi Jeong, Daejeon (KR); Jeong Kyun Kim, Daejeon (KR); Myung Nam Bae, Daejeon (KR); Kang Bok Lee, Daejeon (KR); Sang Yeoun Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 43 days.

(21) Appl. No.: 16/687,907

(22) Filed: Nov. 19, 2019

(65) Prior Publication Data
US 2021/0090418 A1    Mar. 25, 2021

(30) Foreign Application Priority Data
Sep. 20, 2019    (KR) .................... 10-2019-0115864

(51) Int. Cl.
*G08B 21/04*    (2006.01)
*A61B 5/11*    (2006.01)
*A61B 5/00*    (2006.01)
*G06K 9/00*    (2006.01)

(52) U.S. Cl.
CPC .......... *G08B 21/043* (2013.01); *A61B 5/1117* (2013.01); *A61B 5/747* (2013.01); *G08B 21/0446* (2013.01); *G06K 9/00348* (2013.01)

(58) Field of Classification Search
CPC .............. G08B 21/043; G08B 21/0446; G06K 9/00348
See application file for complete search history.

(56) References Cited

U.S. PATENT DOCUMENTS

| 2008/0133277 | A1  | 6/2008 | Jang et al. |
| 2014/0214353 | A1  | 7/2014 | Barfield et al. |
| 2014/0276238 | A1* | 9/2014 | Osorio ................. A61B 5/16 600/595 |
| 2015/0182844 | A1  | 7/2015 | Jang |

FOREIGN PATENT DOCUMENTS

| EP | 2320796 B1 | 8/2017 |
| KR | 10-2016-0052879 A | 5/2016 |
| KR | 10-2017-0037416 A | 4/2017 |
| KR | 10-2019-0056132 A | 5/2019 |

* cited by examiner

*Primary Examiner* — Daniell L Negron
(74) *Attorney, Agent, or Firm* — LRK Patent Law Firm

(57) ABSTRACT

A walking analysis method includes measuring impacts due to floor landing occurring during walking; identifying an impact section before floor landing, a free fall section, and an impact peak section by floor landing in an impact graph over time; analyzing at least one impact-related parameter for the impact section before floor landing, the free fall section, and the impact peak section by floor landing; and determining a walking-related accident type according to a result of analyzing the at least one impact-related parameter. Accordingly, by classifying and detecting a variety of accidents that may actually occur, the main walking characteristics that are dangerous in the actual accident can be extracted.

20 Claims, 16 Drawing Sheets

FIG. 8

| risk level score for each accident type | | | | | |
|---|---|---|---|---|---|
| fall down on the level ground (ground-level fall) | | fall from a high place | | collision | |
| Stuck fall | 2 | Fall down from a chair | 2 | Fall after a collision with a soft object while walking | 2 |
| Slip fall (forward, left or right) | 2.5 | | | | |
| Slip fall (backward) | 3 | | | Fall after a collision with a hard object while walking | 3 |
| Fall in place (forward, backward, left or right) | 2 | Fall down from a chair with a primary impact | 3 | | |
| Sit in a chair and fall down while getting up from the chair (forward, left or right) | 1.5 | | | Fall after a collision with an object while moving in a moving object | 3 |
| Fall down during movement while sitting in a chair | 1 | | | | |

FIG. 9

| AGE_RISK | | BMI_RISK | |
|---|---|---|---|
| age range | score | BMI range | score |
| 65 ~ | 1 | 32 ~ | 1 |
| 40 ~ 65 | 0.8 | 27 ~ 32 | 0.4 |
| 15 ~ 40 | 0 | 22 ~ 27 | 0 |
| ~ 15 | 0.5 | ~ 22 | 0.7 |

FIG. 10

| risk level range | accident determination |
|---|---|
| 5 ~ | emergency |
| 4 ~ 5 | danger |
| 1 ~ 4 | warning |
| ~ 1 | accident suspicion |

WALKING ANALYSIS APPARATUS AND METHOD

CROSS-REFERENCE TO RELATED APPLICATION

This application claims priority to Korean Patent Application No. 10-2019-0115864 filed on Sep. 20, 2019 with the Korean Intellectual Property Office (KIPO), the entire content of which is hereby incorporated by reference.

BACKGROUND

1. Technical Field

The present disclosure relates generally to an apparatus and a method for analyzing walking (or, gait), and more specifically, to a walking analysis apparatus and method capable of identifying various falls and collisions which are associated with pedestrian accidents.

2. Description of Related Art

For accidents such as various falls and collisions that may occur during pedestrian walking or daily life, accurate accident analysis and determination immediately after an accident and prompt response to the accident are important. In particular, the elderly and children often have accidents, and the risk of fatal injury is high. Thus, a lack of proper accident response to the injury or a failure to recognize or neglect the injury may worsen the condition and may result in serious loss of life.

Conventional techniques for responding to pedestrian accidents include using video cameras or attaching inertial devices to the body. In this case, the accident is determined by analyzing movement of the pedestrian in real time using a video camera. However, the technique using the video camera has the disadvantage that necessary devices should be installed in advance, and high cost and space constraints for the installation are caused.

Further, the technology using inertial devices attached to the body was mainly developed to distinguish the fall from the basic daily life behavior. However, such the conventional schemes limited in the fall accidents do not detect various types of accidents according to various environments and circumstances, and thus there is a limit to applying them to real life. Also, in addition to the lack of such the specific classification of accidents, the analysis of the pedestrian risk according to the type of accidents was not properly performed.

In addition, as the conventional manners of notifying the accident to rescuers or guardians, there are a manual report by the user and an automatic report. However, there has been a problem that a separate accident response is required because the report may be canceled due to misjudgement that the accident has a level of risk below which it should be reported or due to user's misunderstanding about accident severity.

SUMMARY

Accordingly, exemplary embodiments of the present disclosure provide a walking analysis method.

Also, exemplary embodiments of the present disclosure provide a waking analysis apparatus using the walking analysis method.

Also, exemplary embodiments of the present disclosure provide a method for providing a walking-related accident response service.

According to an exemplary embodiment of the present disclosure, a walking analysis method may comprise measuring impacts due to floor landing occurring during walking; identifying an impact section before floor landing, a free fall section, and an impact peak section by floor landing in an impact graph over time; analyzing at least one impact-related parameter for the impact section before floor landing, the free fall section, and the impact peak section by floor landing; and determining a walking-related accident type according to a result of analyzing the at least one impact-related parameter.

The at least one impact-related parameter may include one or more of a summation of impact in floor landing section (SIF), a free fall duration (FFD), a Impact Before floor-landing section Peak (IBP), and a Impact Peak section Peak by floor-landing (IPP).

The at least one parameter may include, for the impact section before floor landing, the free fall section, and the impact peak section by floor landing, one or more of an order of the sections, a time duration of each of the sections, body tilts at a start point and an end point of each of the sections, a body tilt variation for each of the sections, and acceleration variation for each of the sections.

The determining of the walking-related accident type may comprise determining whether the walking-related accident type is a ground-level fall, falling from a high place, or a collision by comparing each of SIF, FFD, IBP, and IPP with a threshold for each of SIF, FFD, IBP, and IPP.

When the walking-related accident type is the ground-level fall, the determining of the walking-related accident type may further comprise determining whether the ground-level fall is a stuck fall, a slip fall, or a sit down fall by additionally analyzing a maximum impact of an upper body of a pedestrian before floor landing, a tilt variation of a body of the pedestrian, FFD, and an exposure angle of an insole.

The method may further comprise calculating a risk level based on the determined walking-related accident type and at least one additional information. The method may further comprise analyzing walking characteristics of a pedestrian after an accident event occurs; comparing the walking characteristics after the accident event occurs with walking characteristics before the accident event occurs; and determining whether the pedestrian is abnormal according to the accident event based on a result of the comparison.

The analyzing of the walking characteristics may comprise detecting a change in energies of left and right feet during walking; and detecting a walking pattern according to the change of energies in a section of heel-strike (HS) and a section of toe-off (TO).

The one or more additional information may include a biometric factor, a location factor within a dangerous area, and a user risk group factor.

Furthermore, according to an exemplary embodiment of the present disclosure, a walking analysis apparatus may comprise a processor and a memory storing at least one instruction executable by the processor. Also, when executed by the processor, the at least one instruction may be configured the processor to measure impacts due to floor landing occurring during walking; identify an impact section before floor landing, a free fall section, and an impact peak section by floor landing in an impact graph over time; analyze at least one impact-related parameter for the impact section before floor landing, the free fall section, and the impact peak section by floor landing; and determine a walking-related accident type according to a result of analyzing the at least one impact-related parameter.

The at least one impact-related parameter may include one or more of a summation of impact in floor landing section (SIF), a free fall duration (FFD), a Impact Before floor-landing section Peak (IBP), and a Impact Peak section Peak by floor-landing (IPP).

The at least one parameter may include, for the impact section before floor landing, the free fall section, and the impact peak section by floor landing, one or more of an order of the sections, a time duration of each of the sections, body tilts at a start point and an end point of each of the sections, a body tilt variation for each of the sections, and acceleration variation for each of the sections.

The at least one instruction may be further configured the processor to determine whether the walking-related accident type is a ground-level fall, falling from a high place, or a collision by comparing each of SIF, FFD, IBP, and IPP with a threshold for each of SIF, FFD, IBP, and IPP.

The at least one instruction may be further configured the processor to, when the walking-related accident type is the ground-level fall, determine whether the ground-level fall is a stuck fall, a slip fall, or a sit down fall by additionally analyzing a maximum impact of an upper body of a pedestrian before floor landing, a tilt variation of a body of the pedestrian, FFD, and an exposure angle of an insole.

The at least one instruction may be further configured the processor to calculate a risk level based on the determined walking-related accident type and at least one additional information.

The at least one instruction may be further configured the processor to analyze walking characteristics of a pedestrian after an accident event occurs; compare the walking characteristics after the accident event occurs with walking characteristics before the accident event occurs; and determine whether the pedestrian is abnormal according to the accident event based on a result of the comparison.

The at least one instruction may be further configured the processor to detect a change in energies of left and right feet during walking; and detect a walking pattern according to the change of energies in a section of heel-strike (HS) and a section of toe-off (TO).

The one or more additional information may include a biometric factor, a location factor within a dangerous area, and a user risk group factor.

Furthermore, according to an exemplary embodiment of the present disclosure, a walking-related accident response service method may comprise identifying an impact section before floor landing, a free fall section, and an impact peak section by floor landing in a graph of impacts due to floor landing occurring during walking, determining a walking-related accident type by analyzing at least one impact-related parameter for each of the identified sections; calculating an accident risk level based on at least one of the determined walking-related accident type, a biometric factor, a location factor within a dangerous area, and a user risk group factor; and performing an accident response service according to the calculated accident risk level.

The determining of the walking-related accident type may comprise determining whether the walking-related accident type is a ground-level fall, falling from a high place, or a collision by comparing each of a summation of impact in floor landing section (SIF), a free fall duration (FFD), an impact before floor-landing section peak (IBP), and an impact peak section peak by floor-landing (IPP) with a threshold for each of SIF, FFD, IBP, and IPP.

According to the exemplary embodiments of the present disclosure as described above, by classifying and detecting a variety of accidents that may actually occur, the main walking characteristics that are dangerous in the actual accident can be extracted. The exemplary embodiments of the present disclosure can also calculate the risk level and respond quickly to the accident by comprehensively utilizing user history information, biometric information, and location/dangerous area information based on such the method.

In addition, by responding to the accident by comparing and analyzing the pedestrian's usual walking characteristics and patterns and those of a suspected accident situation, a false alarm rate can be reduced, and serious injuries, which may occur due to incorrect recognition and neglect of the seriousness of the accident, can be prevented. The walking analysis apparatus according to the exemplary embodiments of the present disclosure is inexpensive, small in size, and easy to attach to the body. Also, it is easy to carry on a part of the upper body (e.g., waist, neck, or pocket) or a part of the lower body (e.g., in form of an insole of a shoe).

BRIEF DESCRIPTION OF DRAWINGS

Embodiments of the present disclosure will become more apparent by describing in detail embodiments of the present disclosure with reference to the accompanying drawings, in which:

FIG. 8 is a table illustrating an example of a risk level score for each type of accident according to an exemplary embodiment of the present disclosure;

FIG. 9 is a diagram illustrating an example of a user risk group factor score according to an exemplary embodiment of the present disclosure;

FIG. 10 illustrates an example of an accident determination result for each risk score according to the present disclosure;

Figure 1:
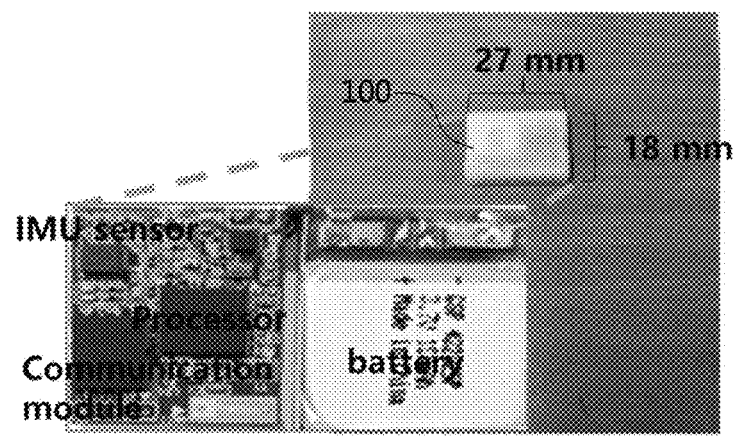
FIG. 1 is a diagram illustrating an appearance of a walking analysis apparatus in a prototype form according to an exemplary embodiment of the present disclosure.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION OF THE EMBODIMENTS

Embodiments of the present disclosure are disclosed herein. However, specific structural and functional details disclosed herein are merely representative for purposes of describing embodiments of the present disclosure. Thus, embodiments of the present disclosure may be embodied in many alternate forms and should not be construed as limited to embodiments of the present disclosure set forth herein.

Accordingly, while the present disclosure is capable of various modifications and alternative forms, specific embodiments thereof are shown by way of example in the drawings and will herein be described in detail. It should be understood, however, that there is no intent to limit the present disclosure to the particular forms disclosed, but on the contrary, the present disclosure is to cover all modifications, equivalents, and alternatives falling within the spirit and scope of the present disclosure. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure classifies and defines various types of accidents that may occur according to various situations in order to be applicable to real life, and proposes an algorithm and method for detecting main walking characteristics through a walking analysis apparatus worn on a pedestrian's body. In addition, by analyzing a risk of the pedestrian according to each type of accidents and responding appropriately, the present disclosure aims to provide a practical and effective pedestrian accident response service.

To this end, the present disclosure newly classifies and defines the accidents occurring during walking or daily life of a pedestrian, based on actual cases of fatal accidents that occur frequently to the general public including the elderly and children. The accidents may be classified into falls such as stumbling over an obstacle, falling down on the level ground (falling forward, backward, left and right), slipping, falling directly from a high place to a ground or falling to the ground with a primary impact on the way, and collisions such as falling to a floor due to a strong collision by external objects (hard or soft objects) during walking or moving in a moving object. These are commonly accidents giving impacts by floor landing (or, falling to the ground).

In other words, exemplary embodiments of the present disclosure extract walking characteristics to classify an accident type and analyze the risk. For this purpose, the present disclosure proposes factors that have not been presented in the prior art. Since the impact of floor landing occurs in case of an accident, in order to distinguish between types of accidents, it may be most important to detect and analyze key sections. Here, the key sections may include a primary impact section in which an upper body or lower body receives a primary impact before a main impact caused by floor landing, a free fall section, and an impact peak section by floor landing. In the present disclosure, the accident types are categorized by using the key sections and the walking characteristics detected in each of key sections. Also, the accidents can be addressed by applying a weighting value to each type of the accidents and by calculating a risk level using biometric information and location/risk information of the pedestrian.

Additionally, in the present disclosure, the walking characteristics and patterns before and after the occurrence of the accident are analyzed. This is to analyze the types of accidents from the perspective of the accident response depending on how dangerous the pedestrian is after the accident and whether or not the pedestrian needs help.

To this end, the present disclosure proposes a newly-defined algorithm for classifying various accident types by extracting the main walking characteristics based on acceleration/gyro sensor data measurement of the pedestrian (or, handicapped), and provides an accident response service through accident analysis and determination, in which weighting values are applied to the respective types of accidents and the risk level is calculated by reflecting user information, biometric information, and location/risk information.

Hereinafter, preferable exemplary embodiments of the present disclosure will be described in detail with reference to the accompanying drawings.

FIG. 1 is a diagram illustrating an appearance of a walking analysis apparatus in a prototype form according to an exemplary embodiment of the present disclosure.

As shown in FIG. 1, a walking analysis apparatus in a prototype form may be manufactured to have a size of 27 mm×18 mm. The walking analysis apparatus according to the present disclosure may comprise components such as a communication module, an Inertial Measurement Unit (IMU) sensor (or, an acceleration/gyro sensor), a processor, and the like. The walking analysis apparatus may be attached to a pedestrian's body to detect an accident occurring in the pedestrian (i.e., user) and detect walking characteristics of the pedestrian.

Figure 2A:
FIGS. 2A to 2C are conceptual diagrams illustrating examples of a walking analysis apparatus attached to a body of a pedestrian according to exemplary embodiments of the present disclosure.
Figure 2B:
Figure 2C:
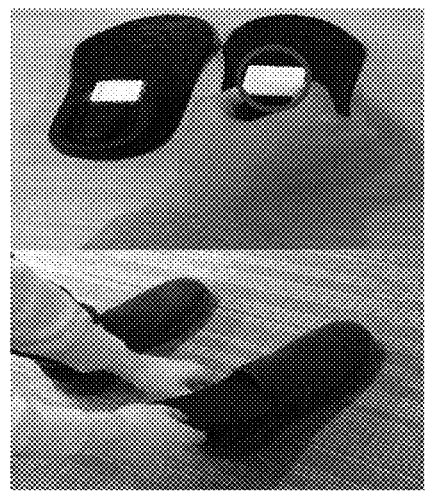

FIGS. 2A to 2C are conceptual diagrams illustrating examples of a walking analysis apparatus attached to a body of a pedestrian according to exemplary embodiments of the present disclosure.

FIG. 2A shows a state in which the walking analysis apparatus according to the present disclosure is mounted on the upper neck portion of the pedestrian, FIG. 2B shows a state in which the walking analysis apparatus according to the present disclosure is mounted on the upper waist portion of the pedestrian, and FIG. 2C shows a state in which the walking analysis apparatus according to the present disclosure is mounted on the foot of the lower body of the pedestrian, that is, the shoe insole.

As such, the walking analysis apparatus according to the present disclosure may be used by being attached to the upper body of the pedestrian (e.g., in form of a necklace, a waistband, a belt, etc.) or the lower body of the pedestrian (e.g., in form of a shoe insole). However, its form or attachment position is not limited to the examples presented through FIGS. 1 and 2A to 2C.

Figure 3:
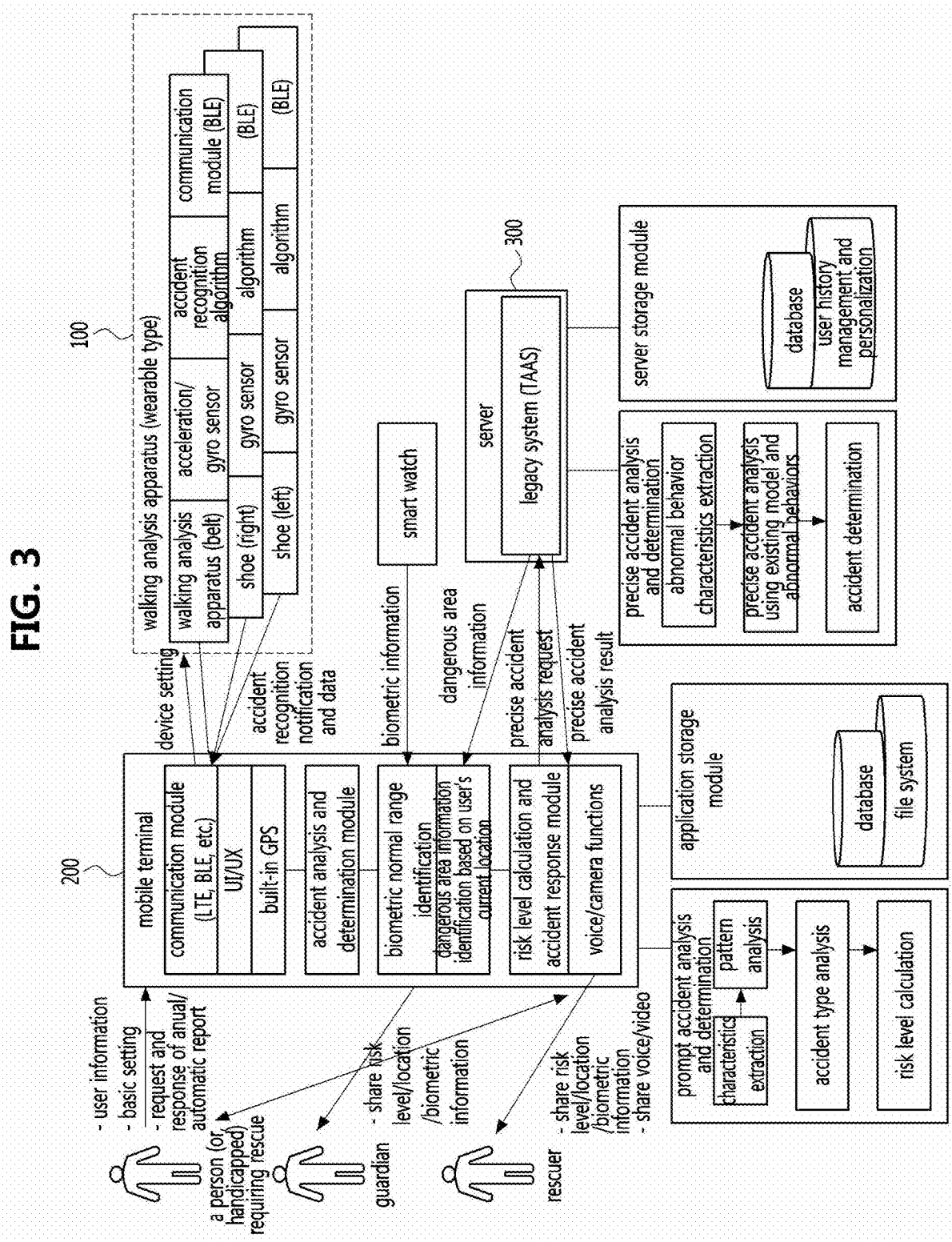
FIG. 3 is a block diagram illustrating a walking analysis system according to an exemplary embodiment of the present disclosure.

FIG. 3 is a block diagram illustrating a walking analysis system according to an exemplary embodiment of the present disclosure.

The walking analysis apparatus 100 according to the present disclosure may operate in conjunction with a mobile terminal 200, a server 300, and the like. In the present disclosure, a system including one or more walking analysis apparatuses 100, the mobile terminal 200, the server 300, and optionally additional equipment such as a smart watch is referred to as a 'walking analysis system'.

The walking analysis apparatus 100 may be mounted on various portions of the pedestrian's body such as, for example, a left shoe, a right shoe, and a belt. The acceleration/gyro sensor of the walking analysis apparatus 100 may collect inertia data to recognize an accident and analyze walking characteristics. The walking analysis apparatus 100 may transmit an accident recognition notification to the mobile terminal, and transmit the collected inertia data and the walking characteristics data to the mobile terminal 200. The mobile terminal may classify and determine the accident type based on the collected data. Each of the mobile terminal and the walking analysis apparatus may have a built-in processor, and may perform a distributed process for judging the walking characteristics and the accident. Therefore, the calculation is quick and battery consumption is efficient.

In addition, the mobile terminal 200 may collect biometric information (heart rate, body temperature, etc.) of the pedestrian from the smart watch, and may determine abnormality of the living body by analyzing how much the biometric value of the pedestrian has changed since the accident time and whether the biometric value is out of a normal range by comparing the biometric information of the pedestrian with the usual. Also, the mobile terminal 200 may compare a current location of the user, which is collected from a built-in GPS, and information of dangerous areas, which is collected by the server 300 in conjunction with an external system of a traffic accident analysis system (TAAS), to determine whether the current location of the user belongs to a dangerous area. The server 300 may perform precise accident analysis by extracting abnormal behaviors or walking characteristics from the data provided by the mobile terminal.

The pedestrian's basic information (e.g., body information, guardian's contact, etc.), configuration information (e.g., device setting information, location/voice/camera/file usage consent information, etc.), accident history information (e.g., accident analysis result, accident response result, etc.), a file log (sensor data, biometric data, location data, etc.), and the like may be stored in an application storage module of the mobile terminal 200 or a storage module of the server 400.

In the present exemplary embodiment, in consideration of the computational burdens, the entity detecting the walking characteristics is described as the walking analysis apparatus, and the entity analyzing the accident type and calculating the risk level is described as the mobile terminal. However, the accident type analysis and risk level calculation may also be performed by the walking analysis apparatus.

In exemplary embodiments of the present disclosure, it is also possible to calculate the risk level and provide an accident response service by combining the above-described information. In case of a manual report or an automatic report, report notification may be transmitted to the guardian and the rescuer (e.g., 119 or 911 rescue center) in common, and when an accident is suspected, precise accident analysis and determination (through comparison between walking characteristics and patterns after the suspected accident and them of usual cases) may be performed, and the result may be informed to the user and the guardian.

Figure 4:
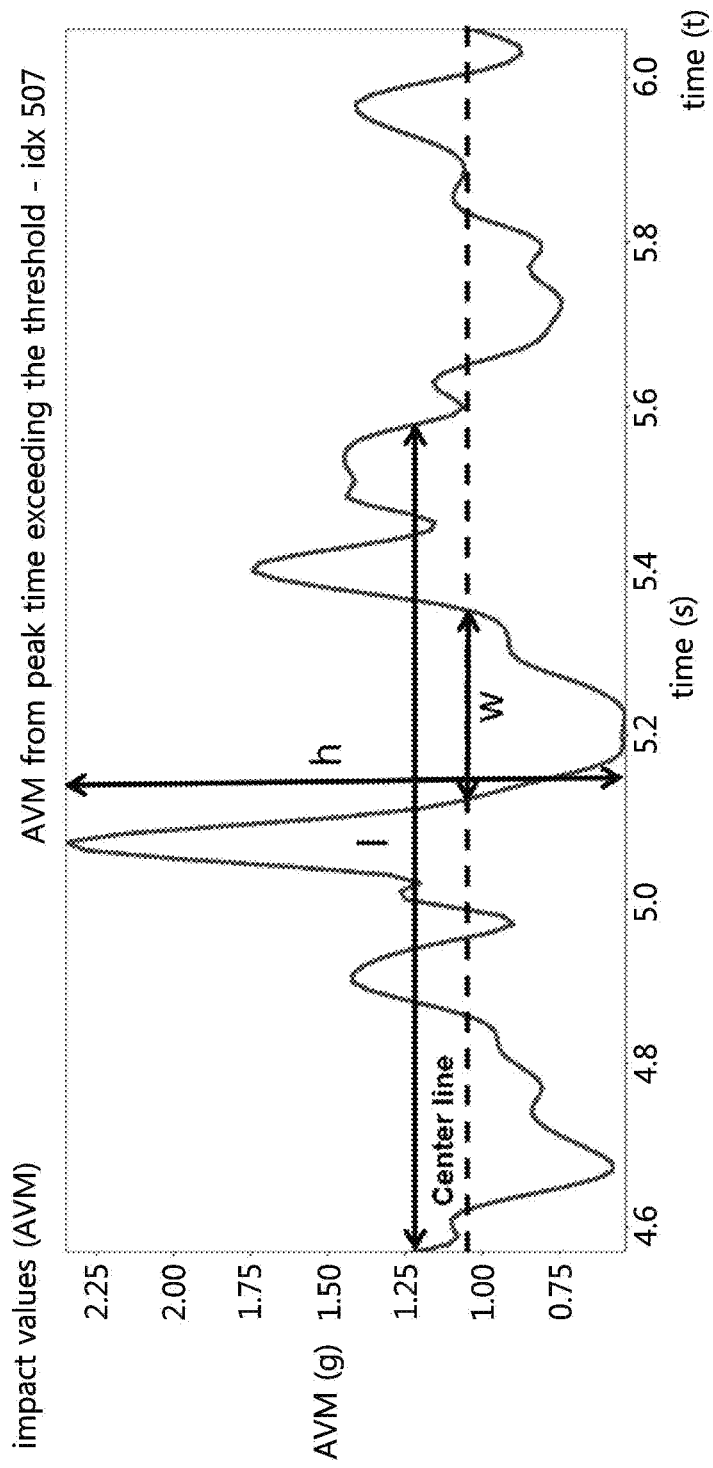
FIG. 4 is a diagram illustrating a curve shape analysis method in a graph showing impacts during walking, which is applied to an exemplary embodiment of the present disclosure.

FIG. 4 is a diagram illustrating a curve shape analysis method in a graph showing impacts during walking, which is applied to an exemplary embodiment of the present disclosure.

In the present disclosure, a method for extracting pedestrian's walking characteristics is based on detecting the impact peak section by floor landing, the free fall section before floor landing, and the primary impact section before floor landing.

Accordingly, the present disclosure provides a method for detecting the impact peak section by floor landing, and detecting a free fall duration before floor landing and the primary impact section before floor landing. The detection of the impact section according to the present disclosure may be performed by calculation based on the impacts (e.g., amplitude vector magnitude (AVM)) over time. Here, the impact applied to the pedestrian by the floor during walking may be represented by a square root of a sum of squares of acceleration values of each axis, which may be expressed as Equation 1 below.

$$\text{Impact value(AVM)} = \sqrt{A_x^2 + A_y^2 + A_z^2} \quad \text{[Equation 1]}$$

The impact value shown in Equation 1 is an acceleration magnitude measured by a 3-axis acceleration sensor. Here, '$A_x$' represents an acceleration value on the x axis, '$A_y$' represents an acceleration value on the y axis, and '$A_z$' represents an acceleration value on the z axis.

The impact peak section by floor landing may be calculated by selectively applying a time threshold analysis method, a curve shape analysis method, a switching analysis method, or the like.

In the time threshold analysis method, when a peak-to-peak interval of the impact before the occurrence of the accident event satisfies a threshold th0 or less, it is regarded as a continuous impact by floor landing. Optionally, the peak-to-peak interval includes a point satisfying 1 g or less. The threshold th0 is a constant value fixed to a certain range (e.g., at most 1 second), and th0 may decrease as the weight of the pedestrian increases.

In the curve shape analysis method, points where the impact is greater than or equal to a threshold th1 before the occurrence of the accident event may be determined, and a height (h), a width (w), and a curve surface parameter (Rku) of a curve between the points may be calculated. When the amount of impact of the curve within a reference length l is Z(x), Rku may mean a value obtained by dividing a trigonometric mean of Z(x) by a third power of Rq.

In FIG. 4, 'h' represents a length between the maximum impact and the minimum value of the valley, and 'w' represents a length between left and right points where a middle value line of the maximum value and the minimum value is intersected with the curve. When the impact amount of the curve is Z(x) within a reference length l, Rku may mean a cubic mean of Z(x) divided by a cube of Rq. Rq may represent a root mean square height and may be calculated as an arithmetic mean of absolute values of differences between Z(x) and a reference centerline.

$$Rku = \frac{1}{Rk^4}\left(\frac{1}{l}\int_0^l z^4(x)dx\right) \quad \text{[Equation 2]}$$

$$Rq = \sqrt{\frac{1}{l}\int_0^l\int_0^l z^2(x)dx}$$

As shown in Equation 3 below, the higher the height and the closer the minimum value of the point-to-point curve is to 0, the smaller a threshold th3 for the width.

$$Th3 = \alpha \times (\min(AVM_{peak\ 0\text{-}peak\ 1}) \times \text{height}(h))^{-1} \quad \text{[Equation 3]}$$

In Equation 3, $\alpha$ is a constant having a value between 0 and 1.

When the height of the curve satisfies a threshold th2 or more and the width satisfies a threshold th3 or less, it is regarded as a continuous impact peak section by floor landing.

On the other hand, in the switching analysis method, if the number of points that are +/−crossed in a section between points where derivative results of the impact graph before the event occurs become greater than or equal to a threshold th4, the corresponding section is regarded as a continuous impact peak section by floor landing.

Figure 5A:
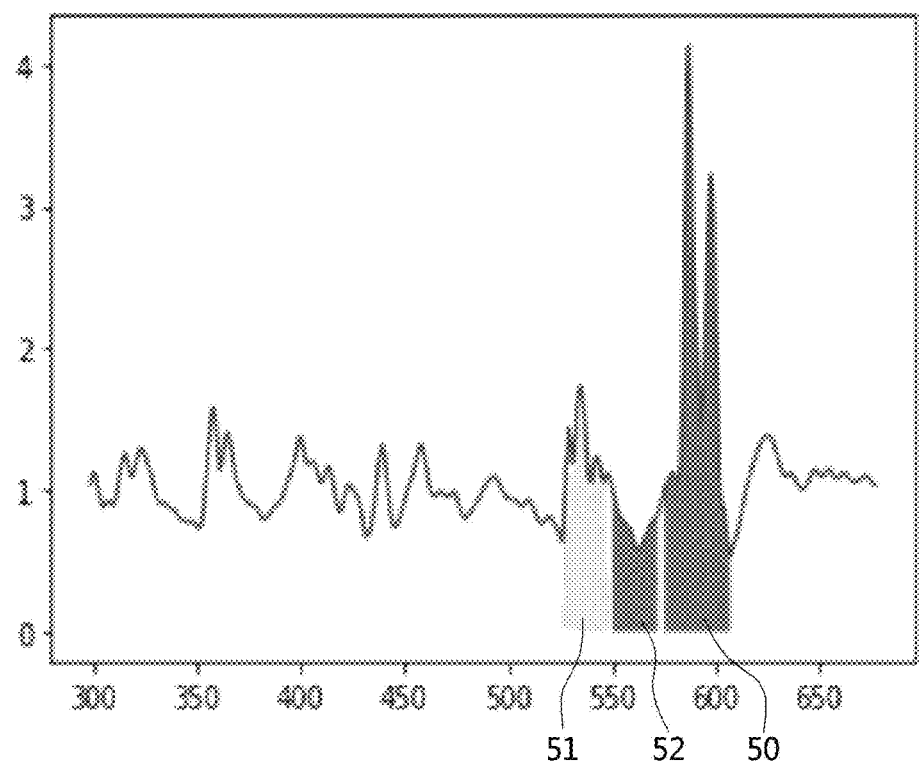
FIGS. 5A and 5B are diagrams illustrating key sections in a graph showing impacts during walking.
Figure 5B:
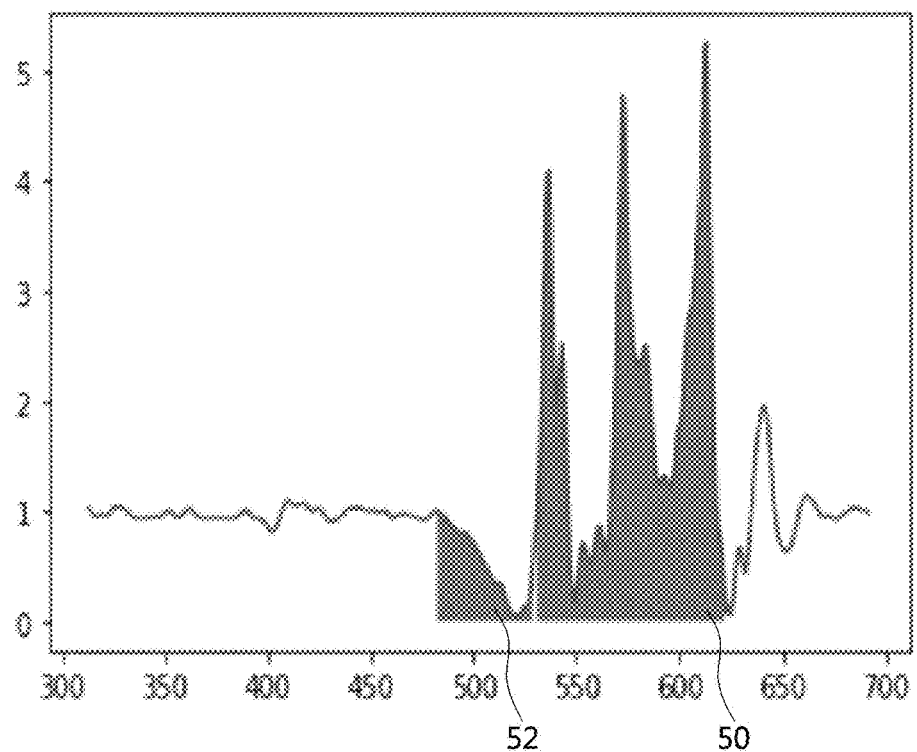

FIGS. 5A and 5B are diagrams illustrating key sections in a graph showing impacts during walking.

Referring to FIG. 5A, in the graph, a primary impact section before floor landing 51 and a free fall section 52 are located before an impact peak section by floor landing 50. These sections may be associated with important characteristics or parameters utilized in walking analysis in accordance with the present disclosure.

The free fall section 52 may occur just before the impact peak section by floor landing. A point of time at which the impact immediately before a first impact peak due to floor landing becomes less than or equal to a threshold th5 may be set as a free fall end point, and a point of time at which the corresponding value becomes more than or equal to a threshold th6 may be set as a free fall start point. Th5 and th6 may be fixed constants in ranges of 1 g~3 g and 0.1 g~1 g, respectively, and a free fall duration (i.e., Free-Fall Time (FFD)) may be more than 0 seconds.

The primary impact section before floor landing 51 may be a section in which the body is shocked before floor landing, and may mean a section from a time point at which the impact becomes greater than or equal to a threshold th7 to a time point at which the impact becomes again less than or equal to the threshold th7. The maximum impact value in the primary impact section before floor landing 51 may be called a maximum primary impact before floor landing (i.e., IPP before floor landing (IBP)), and may be represented by 'IBPwaist' and 'IBPinsole' for the upper and lower bodies, respectively.

Although the graph shown in FIG. 5A includes the primary impact section before floor landing 51 and the free fall section 52 before the impact peak section by floor landing 50, the graph shown in FIG. 5B includes only the free fall section 52 before the impact peak section by floor landing 50, and does not include the primary impact section before floor landing. It may be inferred that the type of impact represented by the graph of FIG. 5A is different from the type of impact represented by the graph of FIG. 5B.

The main characteristics used to determine the type of accident according to the present disclosure are an order of the sections, a time duration of each section, body tilts (e.g., tilt angle point (TAP)) of the start and end points of each section, the amount of the body tilt variation for each section (e.g., tilt variation in each section (TVS)), a summation of impacts due to floor landing (e.g., summation of impact in floor landing section (SIF)), the free fall duration (i.e., FFD), and the Impact Before floor-landing section Peak(i.e., IBPwaist, IBPinsole).

Figure 6:
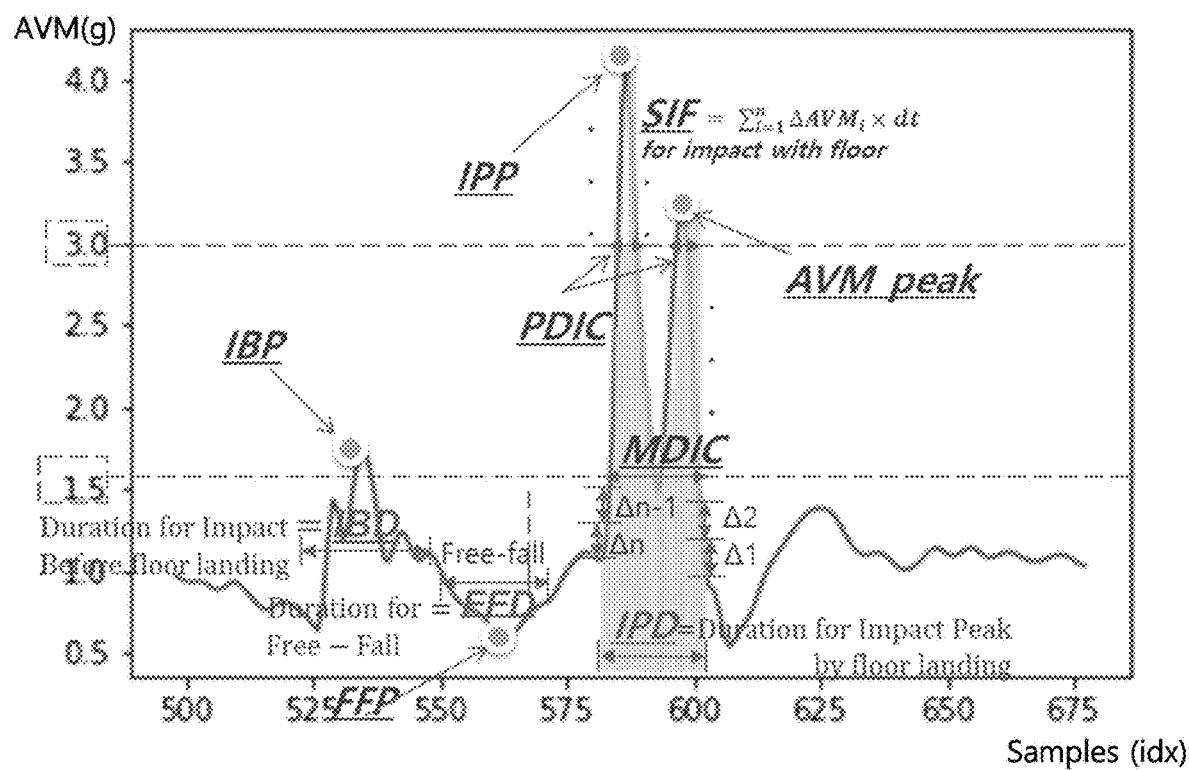
FIG. 6 is a diagram illustrating various parameters used for walking analysis according to the present disclosure in a graph illustrating impact values when walking.

FIG. 6 is a diagram illustrating various parameters used for walking analysis according to the present disclosure in a graph illustrating impact values when walking.

Referring to FIG. 6, the characteristics using the impact (i.e., AVM), which may be additionally used to determine the type of accident in accordance with the present disclosure, may include an impact time (e.g., peak duration index count (PDIC)) by floor landing, a time difference between the impact center points by floor landing (e.g., Middle Impact Duration Index (MDIC)), a minimum impact during the free fall duration (e.g., minimum valley index (MVI)), an average absolute acceleration magnitude variation (AAMV), an impact peak section peak by floor-landing by floor landing (i.e., Impact Peak section Peak by floor-landing (IPP)), an activity ratio index (ARI), and a step count index (SCI) before free fall.

Referring to FIG. 6, IBD stands for impact before floor-landing section duration and IBP stands for impact before floor-landing section peak. Thus, IBP based w can be impact based on waist before floor-landing section peak. Furthermore, FFD is free-fall section duration and FFP is free-fall section peak. IPD stands for impact Peak section Duration by floor-landing, AVM_peak indicates the last peak among peaks equal to or greater than 3 g by floor-landing.

A free fall section average (FFA) may be an average value of AVMs in the free fall section. The AAMV may be a magnitude average of the amount of acceleration variation within a certain time period (window). The ARI may be defined as a ratio of the number of samples whose impact is not more than a specific value (e.g., within a range of 0.8 g~8 g) to the total number of samples in the floor landing. Also, the SCI may be calculated using successive characteristics of valleys and peaks generated by movement before foot rolling.

Figure 7A:
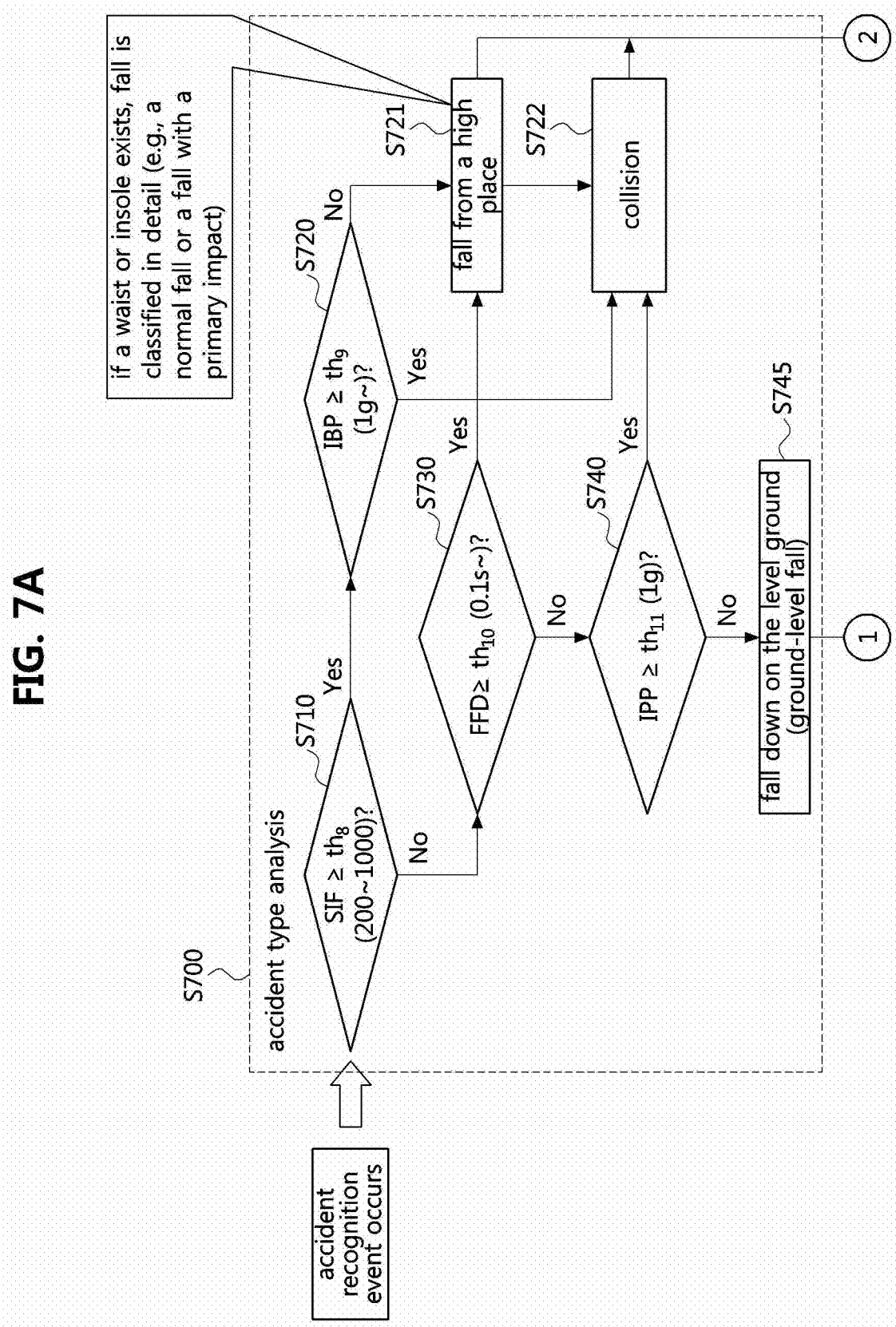
FIGS. 7A and 7B are flowcharts illustrating a method of determining a fall-related accident type according to an exemplary embodiment of the present disclosure.
Figure 7B:
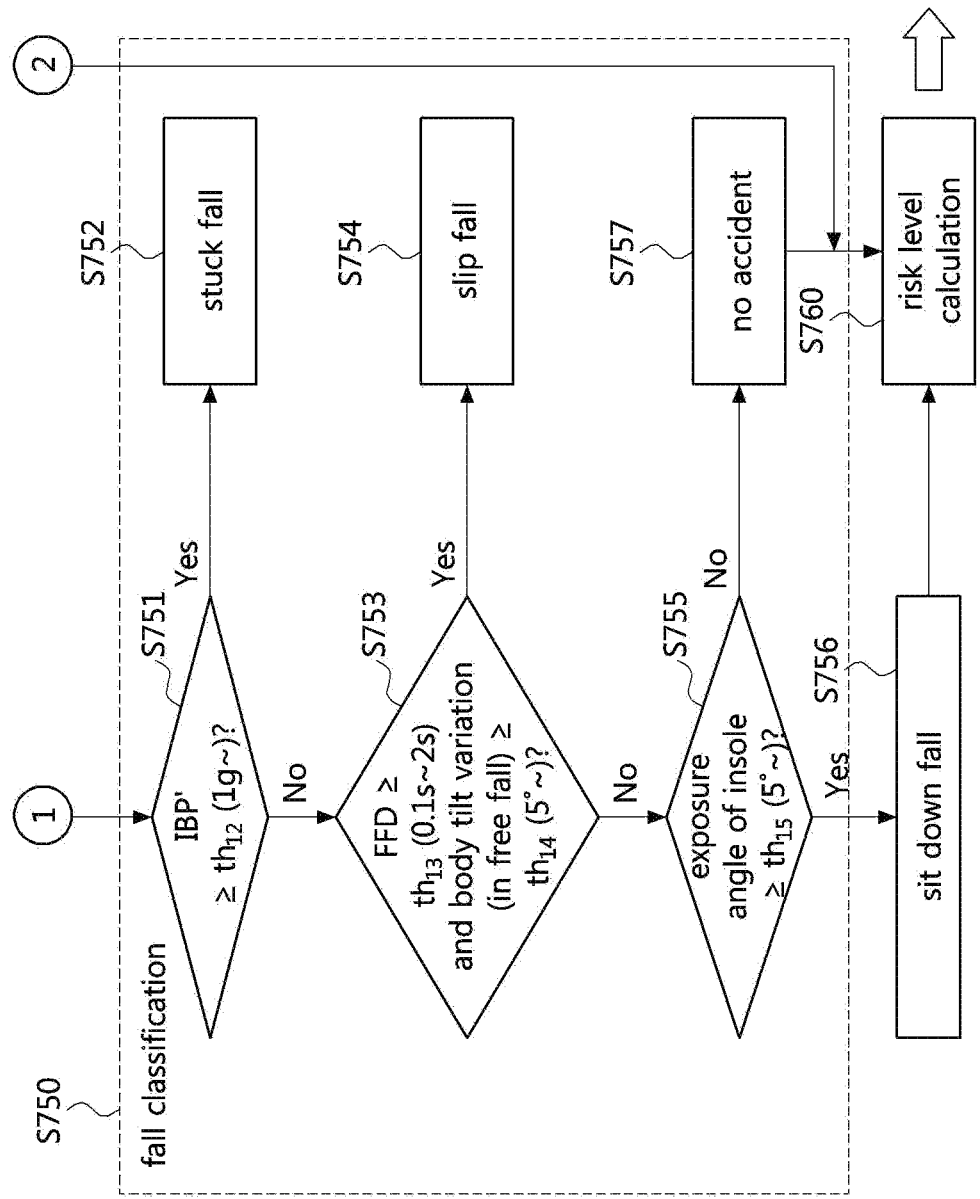

FIGS. 7A and 7B are flowcharts illustrating a method of determining a fall-related accident type according to an exemplary embodiment of the present disclosure.

In the present disclosure, the key sections and the walking characteristics (or parameters) on the graph representing the impact values when walking may be used to determine the accident type. In the present disclosure, the accident types may be largely classified into falling down on the level ground (i.e., ground-level falling (GLF)), falling from a high place, and collisions.

According to the accident type determination method according to an exemplary embodiment of the present disclosure, when an event recognized as an accident occurs, an accident type may be analyzed (S700), and when the accident type is a fall, a procedure for determining the detailed type of the fall may be further performed (S750).

In the procedure S700 of determining the accident type, when the SIF satisfies a threshold th8 or more (example of S710), it may be additionally checked whether the IBP satisfies a threshold th9 or more (S720). When the IBP is greater than or equal to the threshold th9, the accident may be determined as a collision (S722). Otherwise, it may be determined as a fall (S721). Here, the threshold th8 may be in the range of 200 to 1000, for example. Also, the threshold th9 may be 1 g or more.

Here, when the accident is determined as a fall, additional analysis may be performed to distinguish a detailed type of the fall. More specifically, if the walking analysis apparatuses are attached to both the upper body and the lower body, it may be determined whether there is a primary impact before floor landing by comparing the IBPs calculated by the apparatuses attached to the two portions, and it may be determined in detail whether the accident is a normal fall or a case in which a primary impact occurs during the fall.

That is, if the walking-related accident type is a fall, a step of determining whether the accident is a case in which a primary impact exists before floor landing or a free fall from a high place by additionally analyzing the impact value during the free fall, the sum of impact values according to the floor landing, and the amount of body tilt variation may be further performed.

Also, if the walking-related accident type is a collision, a step of determining whether the accident is a collision during moving in a moving object or a collision during walking by additionally analyzing the sum of impacts due to floor landing, the amount of body tilt variation, the amount of variations of the upper and lower bodies of the pedestrian before floor landing, the step count before floor landing, and pedestrian waling statistics information (e.g., acceleration, angular velocity, speed).

On the other hand, returning to the step S710, if the SIF does not satisfy th8 or more (NO in the step S710), it may be determined whether the FFD satisfies a threshold th10 or more (S730). If the FFD is greater than or equal to th10, the accident may be determined as a fall from a high place (S721). On the other hand, determination on IPP may be additionally performed (S740). If the impact maximum value satisfies a threshold th11 or more, it may be determined as a collision (S722). Here, the threshold th10 may be set to a value of 0.1 s or more.

On the contrary, if the impact maximum value does not satisfy a threshold th11 or more, it may be determined as a fall (S745). That is, when the SIF is less than th8, the FFD is less than th10, and the IPP is less than a threshold th11, it may be classified as a fall. The threshold th11 may be set to 1 g, for example.

On the other hand, in the case of being classified as a fall (S745), if both the upper body and the lower body are connected to the walking analysis apparatuses, the type of the fall may be classified in detail.

More specifically, referring to FIG. 7B, in a procedure S750 of classifying the detailed types of falls (S750), when the IBP (i.e., IBP') of the lower body satisfies a threshold th12 or more, the accident may be determined as a 'stuck fall' (S752). On the other hand, if the IBP' of the lower body is less than the threshold th12, it may be determined whether the FFD is greater than or equal to a threshold th13 and whether the TVS is greater than or equal to a threshold th14 (S753). When the FFD is greater than or equal to th13 and the TVS is greater than or equal to th14, the corresponding accident event may be determined as a 'slip fall' (S754). If the FFD is greater than or equal to th13 and the TVS is not greater than or equal to th14 (NO in the step S753), it may be determined whether the TVS of the lower body or an exposure angle of the insole is greater than or equal to a threshold th15 (S755). If the TVS of the lower body or the exposure angle of the insole is equal to or greater than th15, it may be determined as a 'sit down fall' (S756). On the other hand, when the TVS of the lower body part or the exposure angle of the insole is less than th15, it may be determined that there is no accident (S757).

According to another exemplary embodiment of the present disclosure, the accuracy of the above-described accident type determination may be increased by additionally using parameters such as PDIC, MDIC, MVI, AAMV, IPP, ARI, and SCI. The PDIC may be used to distinguish falling surfaces, and the accident may be considered a fall if the PDIC has a value below a certain value (e.g., approximately 50-120 ms). In addition, the MDIC and MVI may be simply used as characteristics for distinguishing an error due to impact to the sensor, and if each satisfies a specific value (e.g., 0.5 s or 0.7 g) or less, the accident may be regarded as a fall. In addition, AAMV, IPP, ARI, and SCI may be used to distinguish daily activities such as simple walking, running, lying down, sitting, and jumping.

The exemplary embodiment illustrated through FIGS. 7A and 7B is just one of the various exemplary embodiments according to the present disclosure, and various changes or modifications to the order of the illustrated steps and the thresholds may be possible.

When the determination of the accident type is completed, a risk level calculation procedure S760 according to the present disclosure may be performed. FIG. 8 is a table illustrating an example of a risk level score for each type of accident according to an exemplary embodiment of the present disclosure.

In the present disclosure, a risk level may be calculated using a total of four factors for the accident type. In the present disclosure, the most basic factor for determining the risk level may be an accident type risk factor. In addition, as three additional factors used to determine the risk level according to the present disclosure, biometric information, location/dangerous area information, and user history information may be used.

Meanwhile, as described above, an accident type classification algorithm may vary, and the accuracy of accident type determination may vary according to a state in which the walking analysis apparatus is mounted (e.g., upper body only, lower body only, both of lower body and lower body, etc.).

Accordingly, an accident type risk factor score according to the present disclosure may be calculated as shown in Equation 4 below by reflecting a score for each accident type and an accuracy of determination for each walking analysis apparatus.

Risk level score for each accident type=risk score for each accident type×determination accuracy (%) [Equation 4]

The calculated risk level score for each accident type may be represented as shown in FIG. 8. Referring to FIG. 8, it may be seen that the risk score may be set differently for each type of accident. In addition, although the risk factor score of the usual falling is lower than that of the falling from a high place or collision, it may be seen that the risk level of slipping or backward falling is high.

Also, an accident risk level (R) according to an exemplary embodiment of the present disclosure may be calculated as a sum of an accident type risk factor score (A), a biological abnormality factor score (B), a location factor score in a dangerous area (C), and a user risk group factor score (D). A range of A may be 0 to 3, and a range of B, C, and D may be 0 to 1.

Therefore, three additional factors, except the accident type risk factor which is the basic factor, may be included in the risk level calculation as independent terms according to whether they can be collected or not.

The biological abnormality factor score (B) may be proportional to a deviation from a normal heart rate or temperature range of a normal person and proportional to a deviation from a normal heart rate or temperature range of a walking person. In addition, an influence degree ($\alpha$) may be determined according to a current pedestrian state (e.g., walking (=1), running (=0.7), exercising (=0.2), moving in a moving object (=1), etc.), and an equation of '$B_{heart\ rate/body\ temperature} = \alpha \times$(a deviation from a normal heart rate/body temperature+a deviation from a daily time heart rate/body temperature)' may be established. In this case, B may be determined as a max ($B_{heart\ rate}$, $B_{body\ temperature}$).

The location in the dangerous area factor score (C) may be given differentially depending on whether the pedestrian's current location is contained within an area where accidents occur frequently or at any other specific location. For example, it may be graded differently depending on whether the pedestrian is on a driveway (e.g., 1 point), on a sidewalk (e.g., 0.5 point), in a building (e.g., 0.1 point), or in his home (e.g., 0 point).

The user risk group factor score (D) may be applied differentially according to an age range and a body mass index (e.g., body mass index (BMI)=(weight (kg)/height (m))$^2$) of the user. This is because actual accidents may be fatal even for small accidents depending on the user's age and obesity.

FIG. 9 is a diagram illustrating an example of a user risk group factor score according to an exemplary embodiment of the present disclosure.

Referring to FIG. 9, the user risk group factor score may be determined according to a risk group factor score for each age range and a risk group factor score for each BMI value.

For example, if an influence ratio of the age group and the body mass index, for the user risk group factor, is 8:2, when they are respectively represent as $\alpha$ and $â$, $\alpha$ may be 0.8, $â$ may be 0.2 ($\because \alpha+â=1$). Also, the risk level D may be expressed as D=$\alpha$ (AGE_RISK)+$â$ (BMI_RISK). Here, 'AGE_RISK' represents the risk group factor score for each age, and 'BMI_RISK' represents the risk group factor score for each BMI value.

FIG. 10 illustrates an example of an accident determination result for each risk score according to the present disclosure.

When the risk level is calculated as described in the previous exemplary embodiment, the accident response may be differentially performed according to the risk level. For example, as illustrated in FIG. 10, the accident determination result may be classified into an accident suspicion, a warning, a danger, and an emergency according to the risk level. In case of the example of FIG. 10, by setting a wide range of scores that may be determined as a warning from the accident determination to induce the pedestrian to report the accident manually, a probability of receiving a false accident report due to false accident determination may be reduced.

Figure 11A:
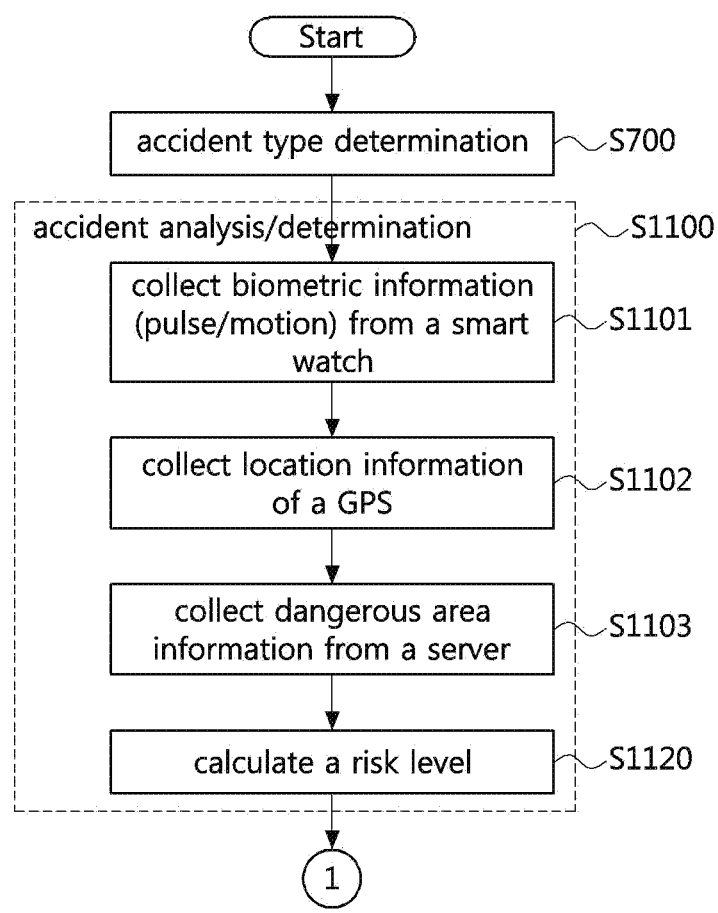
FIGS. 11A and 11B diagrams illustrating an exemplary embodiment of an accident response service method according to a risk level determined according to the present disclosure.
Figure 11B:
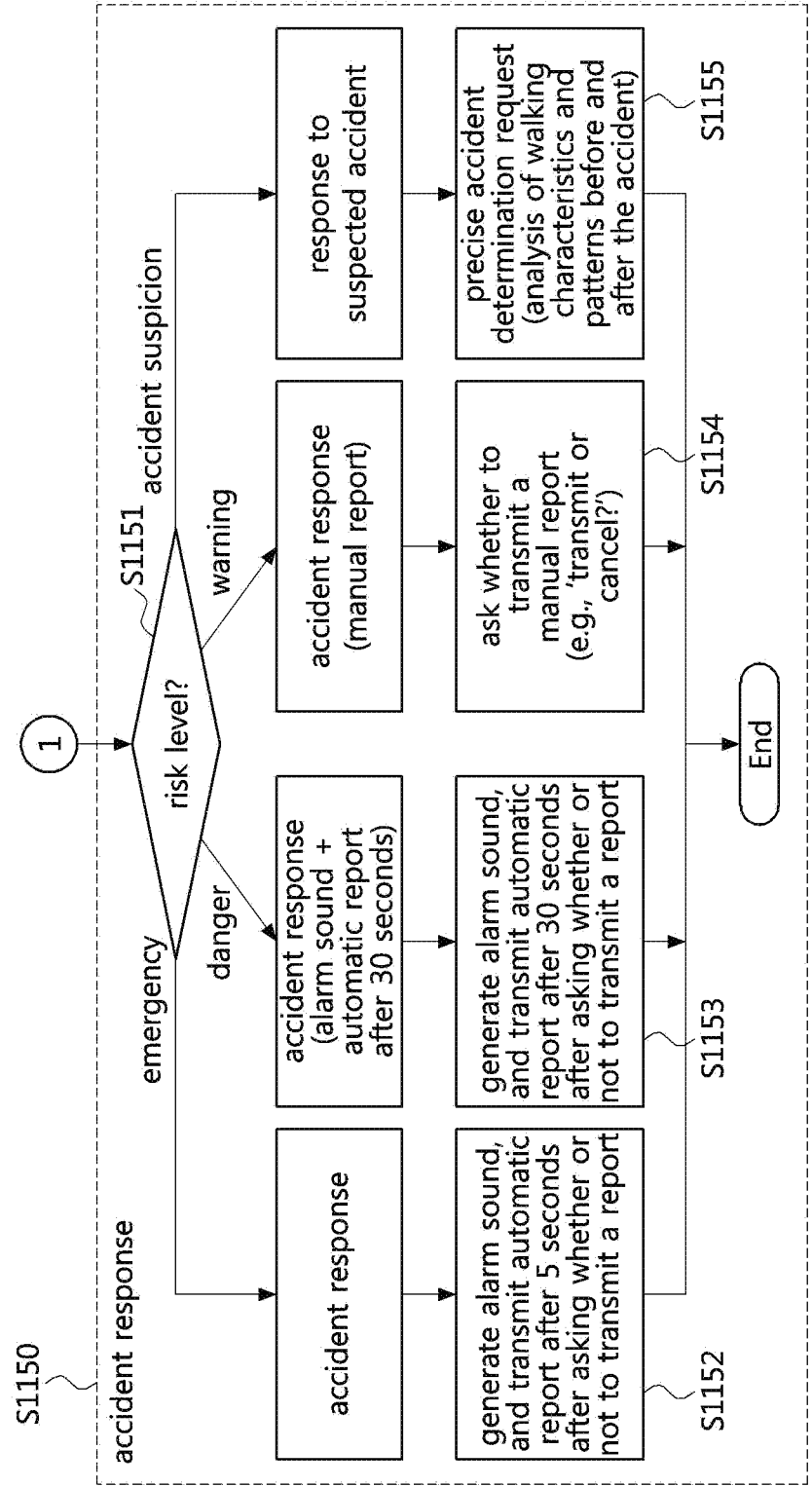

FIGS. 11A and 11B diagrams illustrating an exemplary embodiment of an accident response service method according to a risk level determined according to the present disclosure.

In order to determine a risk level of the accident and to perform an accident response according to the present disclosure, a procedure for determining the type of the accident may be preceded (S700). One preferred exemplary embodiment for determining the type of accident has been presented through FIG. 7.

When the accident type determination is completed, the accident may be analyzed and determined based on the determined accident type (S1100). More specifically, biometric information such as pulse and motion may be collected from an apparatus such as a smart watch or a smart band worn by the pedestrian (S1101). Also, location information may be collected from the GPS of a smartphone possessed by the pedestrian (S1102). Also, information on the dangerous areas may be collected from a guardian server (S1103). Based on the collected biometric information, location information of the pedestrian, information on the dangerous areas, and the like, the risk level may be calculated as described above through the exemplary embodiment (S1120).

Referring to FIG. 11B, after the risk level is calculated (S1151), if the risk level is 'emergency', an emergency accident response may be performed (S1152). That is, the emergency accident situation may be automatically reported within a short time (5 seconds). That is, since the pedestrian may be unconscious or unable to move, a notification sound may be automatically generated to alert the surroundings, and camera/microphone functions may be activated to record video or audio around the accident site.

If the risk level of accident is 'danger', the pedestrian may be notified to make an automatic report within a relatively sufficient time (e.g., 30 seconds), and if the pedestrian does not want to report, the automatic report may be canceled (S1153).

If the risk level of accident is 'warning', the pedestrian may be asked whether the accident is reported or not, and the accident may be manually reported or the report may be canceled (S1154).

Also, if the risk level of accident is 'accident suspicion', analysis of walking characteristics and patterns before and after the occurrence of the accident event may be performed to determine whether the abnormality in the walking has occurred, and notification thereof may be provided to the pedestrian or guardian (S1155).

As such, the accident response service according to the present disclosure may include an abnormal walking analysis before and after the accident. As a result of the risk analysis, when the accident is suspected as an accident having a risk level less than those of accidents which should be reported, the accident may be reported manually or automatically to minimize a false alarm rate. However, in case of canceling the report due to a lack of the awareness of the severity of accident, the walking characteristics and patterns before and after the point of time at which the accident event is recognized may be analyzed.

To this end, the present disclosure, the walking characteristics and patterns may be analyzed and stored before the accident event recognition, that is, on the basis of the acceleration/gyro sensor measurement data collected on a daily basis. Thereafter, when a situation suspected as an accident occurs, the walking characteristics and patterns after the recognition of the accident may be analyzed, and a precise accident determination may be performed by comparing them with those of the usual state. If there is a problem in the walking before and after the suspected accident, the result and reason of the precise determination may be informed to the pedestrian and guardian, thereby responding to the accident.

The walking characteristics may be detected based on the acceleration/gyro sensor data measured from the walking analysis apparatus mounted by the pedestrian described above. Also, the walking patterns may be detected by detecting a balance between left and right feet using statistical and frequency analysis methods.

For example, the statistical analysis method may comprise a step of extract walking linear indexes (e.g., walking speed, walking length, active walking length, single foot support duration, both feet support duration, foot angle) from an acceleration signal and an angular velocity signal, a step of classifying the walking into seven steps (e.g., initial contact, lifting an opposite toe, lifting a heel, opposite initial contact, lifting a toe, approach of both feet, and tibia vertical), and a step of comparing and analyzing the left and right feet by obtaining an average and a variance of the walking linear index for each walking step.

According to a preferred exemplary embodiment of the present disclosure, indicators may be detected through statistical analysis (e.g., average, standard deviation, slope, derivate, integral, maximum, minimum, inflection point, etc. of the acceleration and the angular velocity variation) and frequency analysis (discrete cosine, wavelet, etc.) on a sagittal plane, a coronal plane, and a cross-section plan in the seventh step of walking, and the abnormal walking or behavior of the pedestrian may be determined by comparing the indicators before and after the accident recognition event.

Here, as the frequency analysis, wavelet-based frequency analysis may be used. The frequency analysis method is effective for detecting the walking pattern and the balance between the left and right feet in that the energy changes in the left and right feet during walking can be detected as indicators.

In walking, the greatest energy occurs at a heel-strike (HS) and a toe-off (TO). In order to detect such the points, a continuous wavelet transform (CWT) may be applied to a limited section. This method may identify the change of frequency with time change and may be effectively used to analyze the change of walking pattern before and after the accident.

In this case, various functions may be used as a basis function of the wavelet transform. For example, a Morlet wavelet represented by Equation 5 below may be used.

$$\Psi_0(\eta) = -\pi^{-1/4} e^{i\omega_0 \eta} e^{-\eta^2/2} \qquad \text{[Equation 5]}$$

$$W_n(s) = \sum_{n=-}^{N-1} x_n \Psi^* \left[ \frac{(n'-n)\delta_t}{s} \right]$$

In Equation 5, $\omega_o$ may be a frequency parameter, and $\eta$ may be a time parameter. Here, a CWT coefficient $W_n(s)$ may defined as an inner product of the basis function $\psi^*$ and an acceleration signal $x_n$. (*) denotes a complex conjugate, $\delta t$ denotes the same time interval, s denotes a wavelet scaling factor, and n denotes a current time.

Figure 12:
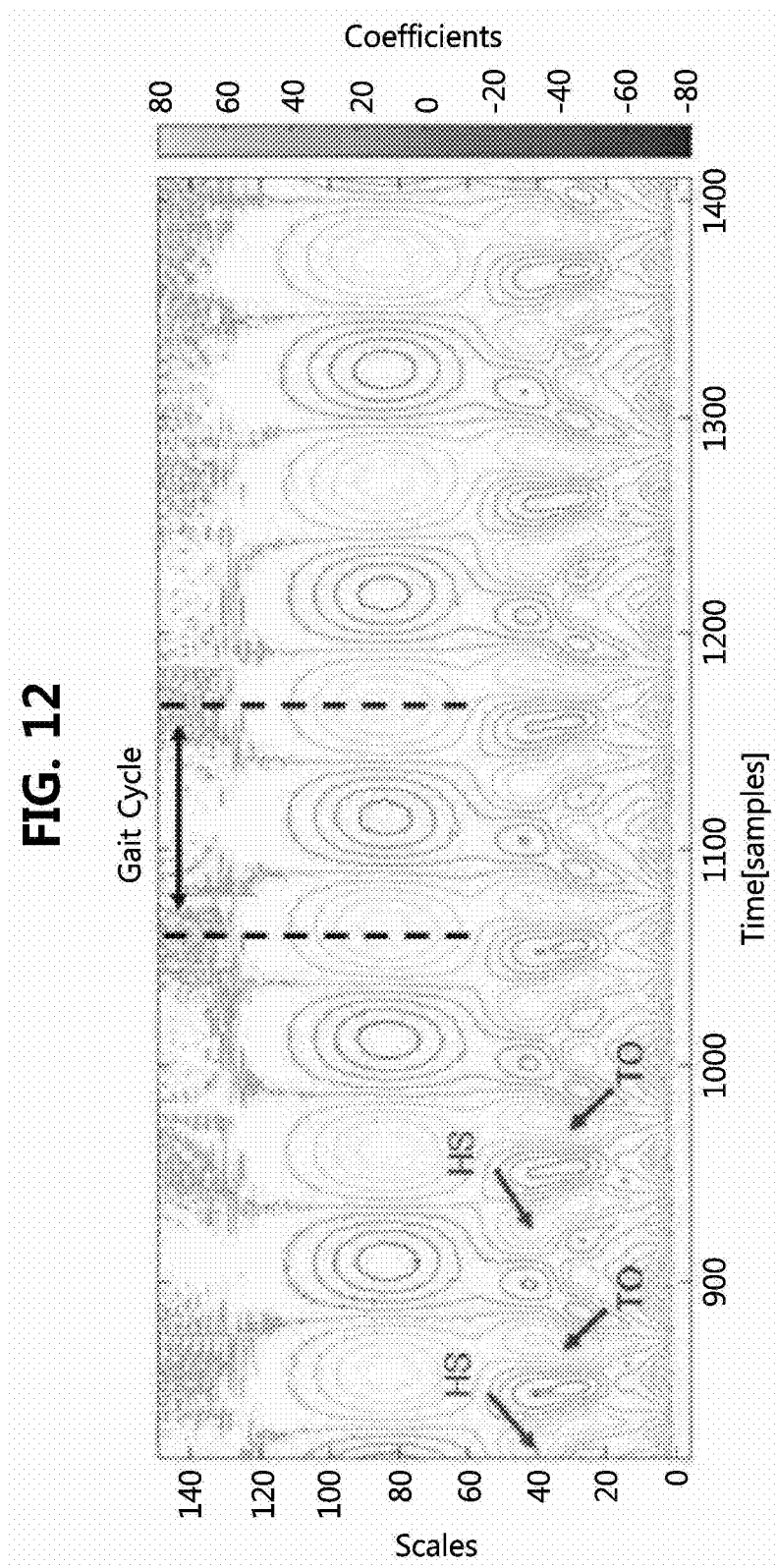
FIG. 12 is a diagram illustrating an example of frequency characteristic analysis of an acceleration signal during walking applied to the present disclosure.

FIG. 12 is a diagram illustrating an example of frequency characteristic analysis of an acceleration signal during walking applied to the present disclosure.

FIG. 12 is a three-dimensional graph showing the CWT coefficients derived by changing the wavelet scaling factor, where a left axis represents scales and a right axis represents the coefficients. As shown in FIG. 12, when an energy density spectrum of the CWT coefficients is calculated, the HS and TO points may be obtained at successive peak points. The scale values of the points where the peak becomes may be usually in a range of 40 to 60 for HS and 20 to 40 for TO.

Figure 13A:
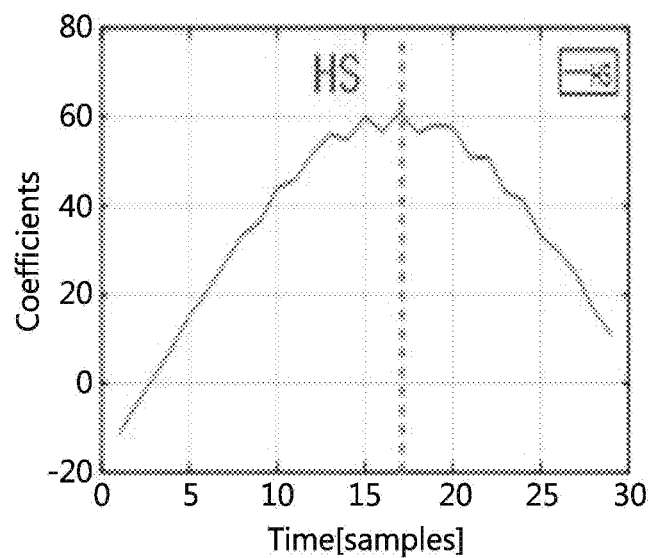
FIG. 13A is a diagram illustrating a change in the CWT coefficients in the HS section in accordance with the present disclosure.
Figure 13B:
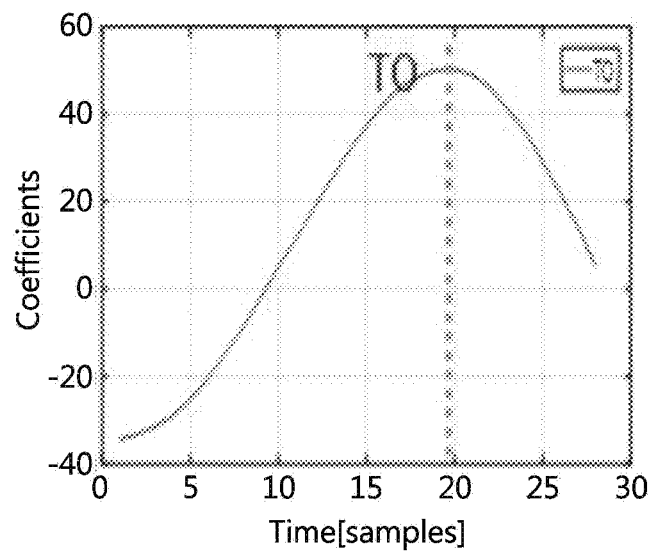
FIG. 13B is a diagram illustrating a change in the CWT coefficients in the TO section in accordance with the present disclosure.

FIG. 13A is a diagram illustrating a change in the CWT coefficients in the HS section in accordance with the present disclosure, and FIG. 13B is a diagram illustrating a change in the CWT coefficients in the TO section in accordance with the present disclosure.

FIGS. 13A and 13B illustrate changes over time of the CWT coefficients when the scale (or amplitude) is fixed in the three-dimensional graph of FIG. 12. FIG. 13A is a graph when the scale is fixed to a value between 40 and 60, which is a typical scale range of the HS, and FIG. 13B is a graph when the scale is fixed to a value between 20 and 40, which is a typical scale range of the TO according to the present disclosure.

In the present disclosure, abnormal signs of the walking pattern may be determined by comparing the CWT coefficient graphs and statistical values in the HS and TO sections in the normal walking and the walking after the accident recognition event.

Figure 14:
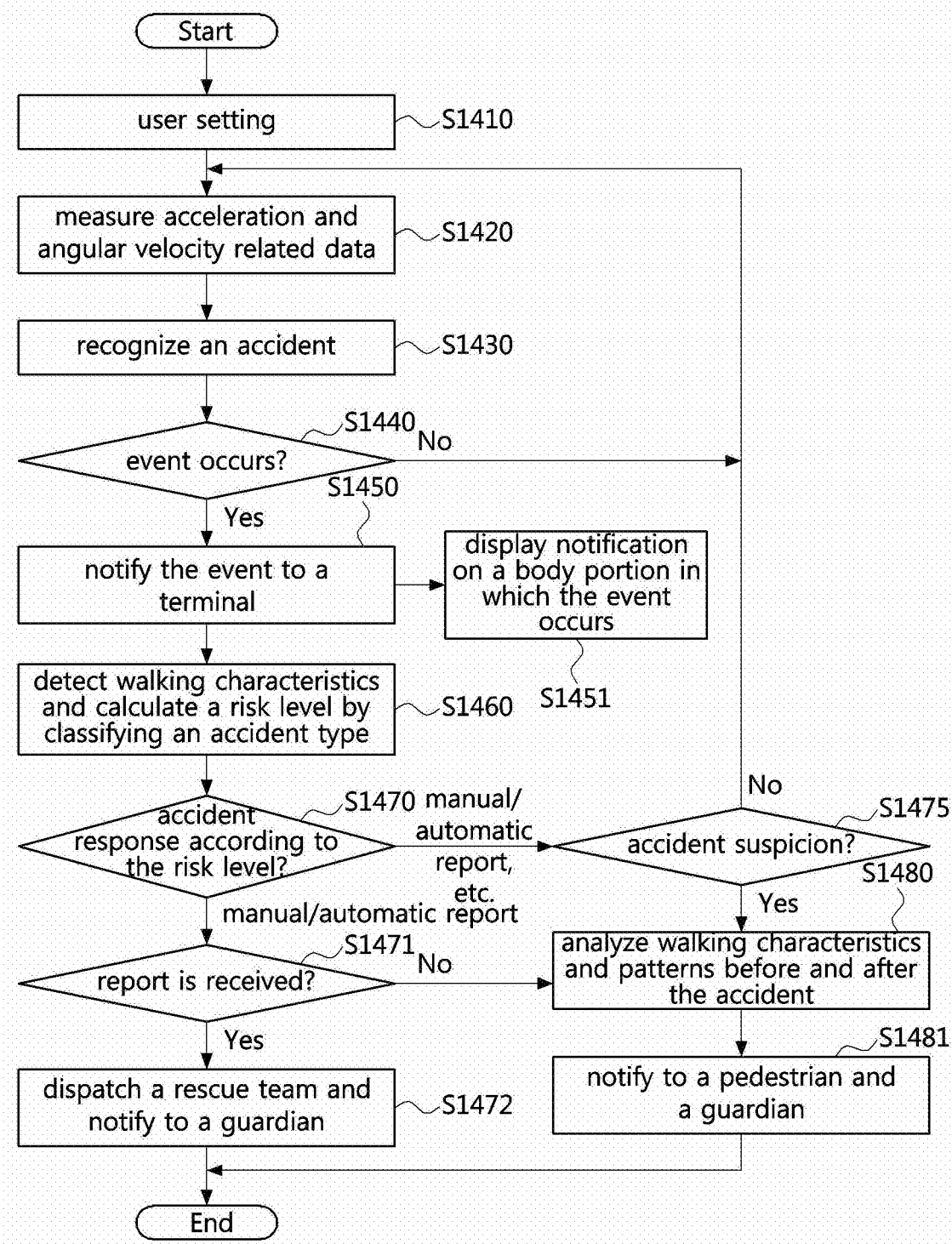
FIG. 14 is a flowchart illustrating a pedestrian accident response service method according to an exemplary embodiment of the present invention.

FIG. 14 is a flowchart illustrating a pedestrian accident response service method according to an exemplary embodiment of the present invention.

The pedestrian accident response service method illustrated in FIG. 14 may be performed by the walking analysis apparatus and the mobile terminal interworking with the walking analysis apparatus described above through the exemplary embodiments of the present disclosure.

When the walking-related accident response service according to the present disclosure is started, user setting related to the service may be performed (S1410). The user setting may be related to setting of the thresholds related to recognition of the accident occurrence. If an impact equal to or greater than a predetermined threshold Th1 occurs and no impact equal to or greater than th1 occurs for a predetermined time Th2 or more thereafter, it may be recognized as an accident. In this case, th1 may be set, for example, in a range of 2 g or more, and th2 may be set, for example, in a range of 0.5 seconds or more.

The walking analysis apparatus may measure acceleration and angular velocity related data (S1420), and recognize an accident based on the set thresholds (S1430). When an accident recognition event occurs (YES in S1440), the walking analysis apparatus may display a notification about a body part in which the event occurs (S1451), and notify the terminal of the accident recognition event (S1450).

At least one walking analysis apparatus attached to the pedestrian's body may detect walking characteristics of the pedestrian (S1460), and transmit the detected walking characteristic data and acceleration/gyro sensor measurement data to the mobile terminal. The mobile terminal may identify an accident type based on the walking characteristics, calculate a risk level, and perform an accident response (S1470). In the present exemplary embodiment, in consideration of the computational burdens, the entity detecting the walking characteristics is described as the walking analysis apparatus, and the entity analyzing the accident type and calculating the risk level is described as the mobile terminal. However, the accident type analysis and risk level calculation may also be performed by the walking analysis apparatus.

When the risk level calculation result indicates a manual report or an automatic report, and the report is received (S1471), a rescue team may be dispatched, and a notification may be transmitted to the guardian (S1472). In addition, when the risk level calculation result indicates suspicion of an accident (YES of S1475) or when the risk level calculation result indicates a manual report or an automatic report, but the user cancels the report without transmitting the report, the walking characteristics and patterns before and after the accident may be analyzed (S1480), and the result thereof may be notified to the pedestrian and the guardian (S1481).

When the accident response service method of the present disclosure described above is summarized in another aspect, the accident response service method according to the present disclosure may be performed by the walking analysis apparatus, and may comprise identifying an impact section before floor landing, a free fall section, and an impact peak section by floor landing in a graph of impacts due to floor landing occurring during walking, determining a walking-related accident type by analyzing at least one impact-related parameter for each of the identified sections; calculating an accident risk level based on at least one of the determined walking-related accident type, a biometric factor, a location factor within a dangerous area, and a user risk group factor; and performing an accident response service according to the calculated accident risk level.

Figure 15:
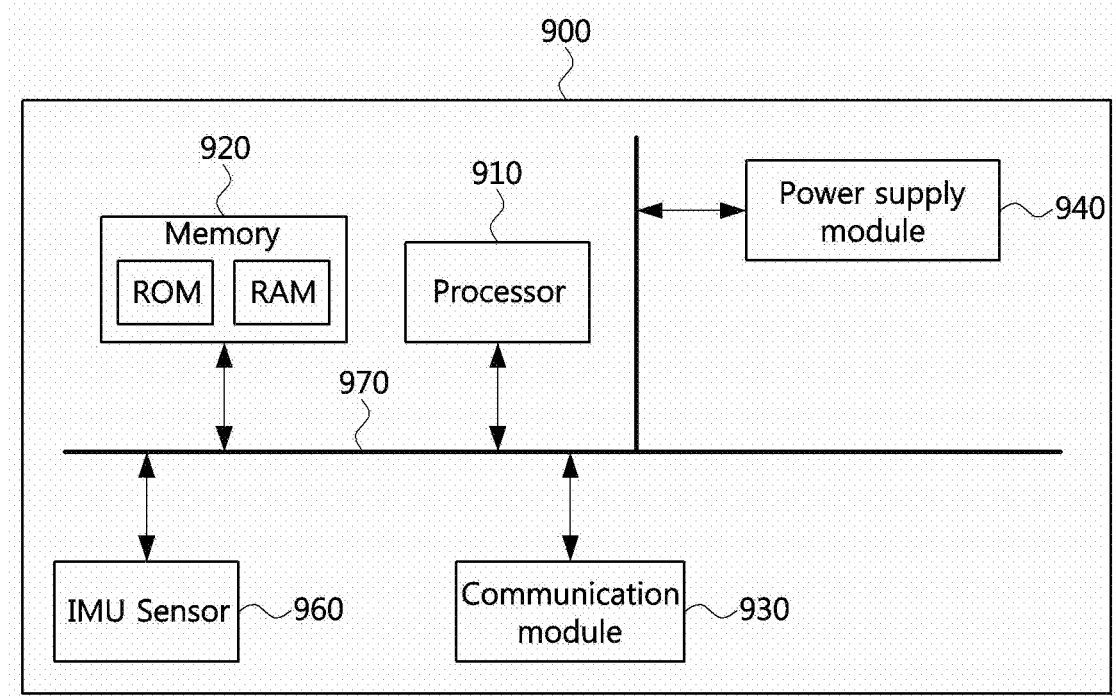
FIG. 15 is a block diagram illustrating a walking analysis apparatus according to another exemplary embodiment of the present disclosure.

FIG. 15 is a block diagram illustrating a walking analysis apparatus according to another exemplary embodiment of the present disclosure.

The walking analysis apparatus according to an exemplary embodiment of the present disclosure may include at least one processor 910, a memory 920 storing at least one instruction executable by the processor, and a communication module 930 connected to a wired or wireless network to perform communication, and an IMU sensor 960 for obtaining acceleration or angular velocity related data generated during walking.

Here, the at least one instruction may be configured the processor to measure impacts due to falling to a floor occurring during walking; identify an impact section before floor landing, a free fall section, and an impact peak section by floor landing in an impact graph over time; analyze at least one impact-related parameter for the impact section before floor landing, the free fall section, and the impact peak section by floor landing; and determine a walking-related accident type according to a result of analyzing the at least one impact-related parameter.

The walking analysis apparatus 900 may further include a power supply module 940 for supplying power to the processor 910, the memory 920, and the communication module 930. The components included in the walking analysis apparatus 900 may be connected by a bus 970 to communicate with each other.

The processor 910 may execute a program command stored in the memory 920. The processor 910 may refer to a central processing unit (CPU), a graphics processing unit (GPU), or a dedicated processor on which methods according to exemplary embodiments of the present disclosure are performed. The memory 920 may be configured of at least one of a volatile storage medium and a nonvolatile storage medium. For example, the memory 920 may be configured as at least one of read only memory (ROM) and random access memory (RAM).

The method according to the exemplary embodiments of the present disclosure may also be embodied as computer readable programs or codes on a computer readable recording medium. The computer readable recording medium is any data storage device that may store data which can be thereafter read by a computer system. The computer readable recording medium may also be distributed over network coupled computer systems so that the computer readable code is stored and executed in a distributed fashion.

In addition, examples of the computer-readable recording medium may include magnetic media such as hard discs, floppy discs, and magnetic tapes, optical media such as compact disc-read-only memories (CD-ROMs), digital video disc (DVDs), and so on, magneto-optical media such as floptical discs, and hardware devices specially configured (or designed) for storing and executing program commands, such as ROMs, random access memories (RAMs), flash memories, and so on. Examples of a program command may not only include machine language codes, which are created by a compiler, but may also include high-level language codes, which may be executed by a computer using an interpreter, and so on.

Some aspects of the present disclosure have been described in the context of an apparatus but may also represent the corresponding method. Here, a block or the apparatus corresponds to an operation of the method or a characteristic of an operation of the method. Likewise, aspects which have been described in the context of the method may be indicated by the corresponding blocks or items or characteristics of the corresponding apparatus. Some or all of operations of the method may be performed by (or using) a hardware device, such as a microprocessor, a programmable computer, or an electronic circuit. In some embodiments, one or more important steps of the method may be performed by such a device. In the exemplary embodiments of the present disclosure, a programmable logic device (e.g., a field-programmable gate array (FPGA)) may be used to perform some or all of functions of the above-described methods. In the exemplary embodiments, the FPGA may operate in combination with a microprocessor for performing one of the above-described methods. In general, the methods may be performed by any hardware device.

While the exemplary embodiments of the present disclosure and their advantages have been described in detail, it should be understood that various changes, substitutions and alterations may be made herein without departing from the scope of the disclosure.

What is claimed is:

1. A walking analysis method comprising:
   measuring impacts due to floor landing occurring during walking;
   identifying an impact section before floor landing, a free fall section, and an impact peak section by floor landing in an impact graph over time;
   analyzing at least one impact-related parameter for each of the impact section before floor landing, the free fall section, and the impact peak section by floor landing; and
   determining whether a walking-related accident type is a ground-level fall, falling from a high place, or a collision according to the analysis of the at least one impact-related parameter.

2. The walking analysis method according to claim 1, wherein the at least one impact-related parameter includes one or more of a summation of impact in floor landing section (SIF), a free fall duration (FFD), an impact before floor-landing section peak (IBP), and an impact peak section peak by floor-landing (IPP).

3. The walking analysis method according to claim 2, wherein the at least one impact-related parameter includes, for the impact section before floor landing, the free fall section, and the impact peak section by floor landing, one or more of an order of the sections, a time duration of each of the sections, body tilts at a start point and an end point of each of the sections, a body tilt variation for each of the sections, and acceleration variation for each of the sections.

4. The walking analysis method according to claim 2, wherein the determining whether the walking-related accident type is the ground-level fall, the falling from a high place, or the collision is made by comparing each of SIF, FFD, IBP, and IPP with a threshold for each of SIF, FFD, IBP, and IPP.

5. The walking analysis method according to claim 4, wherein, when the walking-related accident type is the ground-level fall, the determining of the walking-related accident type further comprises determining whether the ground-level fall is a stuck fall, a slip fall, or a sit down fall by additionally analyzing a maximum impact of an upper body of a pedestrian before floor landing, a tilt variation of a body of the pedestrian, FFD, and an exposure angle of an insole.

6. The walking analysis method according to claim 1, further comprising calculating a risk level based on the determined walking-related accident type and at least one additional information.

7. The walking analysis method according to claim 1, further comprising:
   analyzing walking characteristics of a pedestrian after an accident event occurs;
   comparing the walking characteristics after the accident event occurs with walking characteristics before the accident event occurs; and
   determining whether the pedestrian is abnormal according to the accident event based on a result of the comparison.

8. The walking analysis method according to claim 7, wherein the analyzing of the walking characteristics comprises:
   detecting a change in energies of left and right feet during walking; and
   detecting a walking pattern according to the change of energies in a section of heel-strike (HS) and a section of toe-off (TO).

9. The walking analysis method according to claim 6, wherein the one or more additional information includes a biometric factor, a location factor within a dangerous area, and a user risk group factor.

10. A walking analysis apparatus comprising a processor and a memory storing at least one instruction executable by the processor, wherein when executed by the processor, the at least one instruction is configured to:
    measure impacts due to floor landing occurring during walking;
    identify an impact section before floor landing, a free fall section, and an impact peak section by floor landing in an impact graph over time;
    analyze at least one impact-related parameter for each of the impact section before floor landing, the free fall section, and the impact peak section by floor landing; and
    determine whether a walking-related accident type is a ground-level fall, falling from a high place, or a collision according to the analysis of the at least one impact-related parameter.

11. The walking analysis apparatus according to claim 10, wherein the at least one impact-related parameter includes one or more of a summation of impact in floor landing section (SIF), a free fall duration (FFD), an impact before floor-landing section peak (IBP), and an impact peak section peak by floor-landing (IPP).

12. The walking analysis apparatus according to claim 11, wherein the at least one impact-related parameter includes, for the impact section before floor landing, the free fall section, and the impact peak section by floor landing, one or more of an order of the sections, a time duration of each of the sections, body tilts at a start point and an end point of each of the sections, a body tilt variation for each of the sections, and acceleration variation for each of the sections.

13. The walking analysis apparatus according to claim 11, wherein the at least one instruction is further configured to determine whether the walking-related accident type is the ground-level fall, the falling from a high place, or the collision by comparing each of SIF, FFD, IBP, and IPP with a threshold for each of SIF, FFD, IBP, and IPP.

14. The walking analysis apparatus according to claim 13, wherein the at least one instruction is further configured to, when the walking-related accident type is the ground-level fall, determine whether the ground-level fall is a stuck fall, a slip fall, or a sit down fall by additionally analyzing a maximum impact of an upper body of a pedestrian before floor landing, a tilt variation of a body of the pedestrian, FFD, and an exposure angle of an insole.

15. The walking analysis apparatus according to claim 10, wherein the at least one instruction is further configured to calculate a risk level based on the determined walking-related accident type and at least one additional information.

16. The walking analysis apparatus according to claim 10, wherein the at least one instruction is further configured to:
    analyze walking characteristics of a pedestrian after an accident event occurs;
    compare the walking characteristics after the accident event occurs with walking characteristics before the accident event occurs; and
    determine whether the pedestrian is abnormal according to the accident event based on a result of the comparison.

17. The walking analysis apparatus according to claim 16, wherein the at least one instruction is further configured to:
    detect a change in energies of left and right feet during walking; and detect a walking pattern according to the change of energies in a section of heel-strike (HS) and a section of toe-off (TO).

18. The walking analysis apparatus according to claim 15, wherein the one or more additional information includes a biometric factor, a location factor within a dangerous area, and a user risk group factor.

19. A walking-related accident response service method comprising:
- identifying an impact section before floor landing, a free fall section, and an impact peak section by floor landing in a graph of impacts due to floor landing occurring during walking,
- determining whether a walking-related accident type is a ground-level fall, falling from a high place, or a collision by analyzing at least one impact-related parameter for each of the identified sections;
- calculating an accident risk level based on at least one of the determined walking-related accident type, a biometric factor, a location factor within a dangerous area, and a user risk group factor; and
- performing an accident response service according to the calculated accident risk level.

20. The walking-related accident response service method according to claim 19, wherein the determining whether the walking-related accident type is the ground-level fall, the falling from a high place, or the collision is made by comparing each of a summation of impact in floor landing section (SIF), a free fall duration (FFD), an impact before floor-landing section peak (IBP), and an impact peak section peak by floor-landing (IPP) with a threshold for each of SIF, FFD, IBP, and IPP.

* * * * *